(12) United States Patent
Maddalena et al.

(10) Patent No.: US 9,706,911 B2
(45) Date of Patent: Jul. 18, 2017

(54) VISION TESTING FOR ASTIGMATISM

(71) Applicant: AiVision Pty Ltd, Rockdale (AU)

(72) Inventors: Desmond John Maddalena, Kirrawee (AU); Simon Grbevski, Oatley (AU)

(73) Assignee: AIVISON PTY LTD, Rockdale (AU)

( * ) Notice: Subject to any disclaimer, the term of this patent is extended or adjusted under 35 U.S.C. 154(b) by 0 days.

(21) Appl. No.: 14/959,092

(22) Filed: Dec. 4, 2015

(65) Prior Publication Data

US 2016/0157711 A1     Jun. 9, 2016

(51) Int. Cl.
  *A61B 3/02*    (2006.01)
  *A61B 3/00*    (2006.01)
  *A61B 3/036*   (2006.01)
  *A61B 3/032*   (2006.01)

(52) U.S. Cl.
  CPC ............ *A61B 3/036* (2013.01); *A61B 3/0025* (2013.01); *A61B 3/0033* (2013.01); *A61B 3/032* (2013.01)

(58) Field of Classification Search
  USPC ................................................ 351/200–246
  See application file for complete search history.

(56) References Cited

U.S. PATENT DOCUMENTS

| | | | | |
|---|---|---|---|---|
| 6,386,707 B1* | 5/2002 | Pellicano | ............... | A61B 3/024 351/237 |
| 2004/0064376 A1* | 4/2004 | Yoshida | ................ | A61B 3/032 705/26.8 |
| 2005/0083485 A1* | 4/2005 | Toshima | .............. | A61B 3/0033 351/239 |
| 2008/0018858 A1* | 1/2008 | Kanazawa | ............. | A61B 3/032 351/239 |
| 2014/0268060 A1 | 9/2014 | Lee et al. | | |

FOREIGN PATENT DOCUMENTS

WO        02/00105 A1    1/2002

\* cited by examiner

*Primary Examiner* — Mohammed Hasan
(74) *Attorney, Agent, or Firm* — Kilpatrick Townsend & Stockton LLP (57) ABSTRACT

Disclosed are computer implemented methods for testing astigmatism which display differently colored bars against a contrasting background. In one implementation, parallel colored bars are separated and joined through various angles of rotation against a constant background. In another implementation one set of bars is formed by variable grating pattern which is rotated within an annulus of solid color bars, desirably against a contrasting intermediate background and a reference background having a linear grating pattern.

17 Claims, 7 Drawing Sheets

VISION TESTING FOR ASTIGMATISM

REFERENCE TO RELATED PATENT APPLICATION(S)

This application claims benefit under 35 U.S.C. §119 of the filing date of Australian Patent Application No. 2014904932, filed Dec. 5, 2014, hereby incorporated by reference in its entirety as if fully set forth herein.

TECHNICAL FIELD

The present invention relates generally to vision testing and, in particular, to the automated, or assisted-automation, of astigmatism tests.

BACKGROUND

International Patent Publication No. WO 02/00105 (PCT/AU01/00775) disclosed a system for the testing of human eyesight that was substantially automated and which could be performed by the human subject using an appropriately programmed general purpose computer and without the need for or use of lenses interposed between the subject and a video display screen of the computer. The system operated by executing one or more application programs on the computer and, through interaction between the subject and sequences of graphical images displayed on the display screen by the executing programs, the computer would record the subject's responses. The recording of the responses guided the execution of selected programs to capture detailed test data equivalent to that which would traditionally be recorded by an optometrist performing a traditional eyesight examination with the aid of interposed lenses.

The testing regimen firstly involved a setup phase which essentially calibrated the optical system formed by the subject and the display screen. Specific tests performed included an acuity white E test, various astigmatism tests, near and distance acuity tests, a prefilter contrast test, a discrimination test, binocular tests, a saccades test as well as tests for cataracts, macular integrity, peripheral field and colour vision. The recorded data would be processed by the computer or remotely to calculate at least one aspect of the visual functioning of the subject to thereby enable determination of an optical corrective lens prescription suitable for the subject. The determination could be fully automated by computerised processing, assisted by a skilled optometrist, or performed in whole by the optometrist.

The system enabled subjects at home or in community clinics, for example, to directly access and benefit from vision testing without a need to visit an optometrist or involving the use of expensive lenses.

Astigmatism is a condition where a person's sight levels are in constant conflict for distance and near vision, with the eye reaching a point of equal blurring when neither distance nor close vision is perfectly clear. There is an irregularity to the optical surfaces of the eye that causes blurriness at all distances. The defect is similar to the distortion seen when looking through a cylindrical lens. Any lines seen through the lens that are near to parallel with the cylindrical lenses axis are seen as black, while any lines at an angle to the axis are blurred to a grey colour. This was shown in FIG. 10B of WO 02/00105, where the line 1010 indicated the axis of astigmatism.

Accuracy in any test procedure is always important. This is particularly so for astigmatism tests since astigmatism affects much of the population with less than perfect eyesight.

SUMMARY

The present inventors have devised new astigmatism tests, compared to those disclosed in WO 02/00105, which represent a more accurate means for assessing astigmatic components of the eye. The presently disclosed tests may be used as alternatives to, or in addition to, the tests disclosed in WO 02/00105.

Disclosed are computer implemented methods for testing astigmatism which display differently coloured bars against a contrasting background. In one implementation, parallel coloured bars are separated and joined through various angles of rotation. In another implementation one set of bars is formed by variable grating pattern which is rotated within an annulus of solid colour bars, desirably against a contrasting intermediate background and a reference background having a linear grating pattern.

According to a first aspect of the present disclosure, there is provided a computer implemented method of testing astigmatism of a subject. The method displays on a display device a graphical user interface including a plurality of differently coloured parallel bars in an initial position against a contrasting background. Movement of the bars is controlled, by a subject of the test, from the initial position to cause at least one of a separation of the bars and joining of the bars. The method detects an indication of the subject of separation and joining of the bars respectively, records a measure of movement of the bars from the initial position to the detected indication.

According to a second aspect of the present disclosure, there is provided a computer implemented method of testing astigmatism of a subject. The method displays on a display device a graphical user interface including (i) an annulus of radial lines against a contrasting background, and (ii) a circular contrast grating pattern within the annulus of radial lines. The method controls an angle of rotation of the circular grating pattern within the annulus in response to an input of the subject and detects an indication of a maximal contrast between the circular grating pattern and the annulus of radial lines. The method records the angle of rotation corresponding to the detected indication as the angle of astigmatism of the subject.

Other aspects are also disclosed.

BRIEF DESCRIPTION OF THE DRAWINGS

Some aspects of the prior art and at least one embodiment of the present invention will now be described with reference to the drawings, in which.

DETAILED DESCRIPTION INCLUDING BEST MODE

It is to be noted that the discussions contained in the "Background" section and that above relating to prior art arrangements relate to discussions of documents or devices which form public knowledge through their respective publication or use. Such should not be interpreted as a representation by the present inventor(s) or the patent applicant that such documents or devices in any way form part of the common general knowledge of ordinary skilled persons in the art.

Figure 1A:
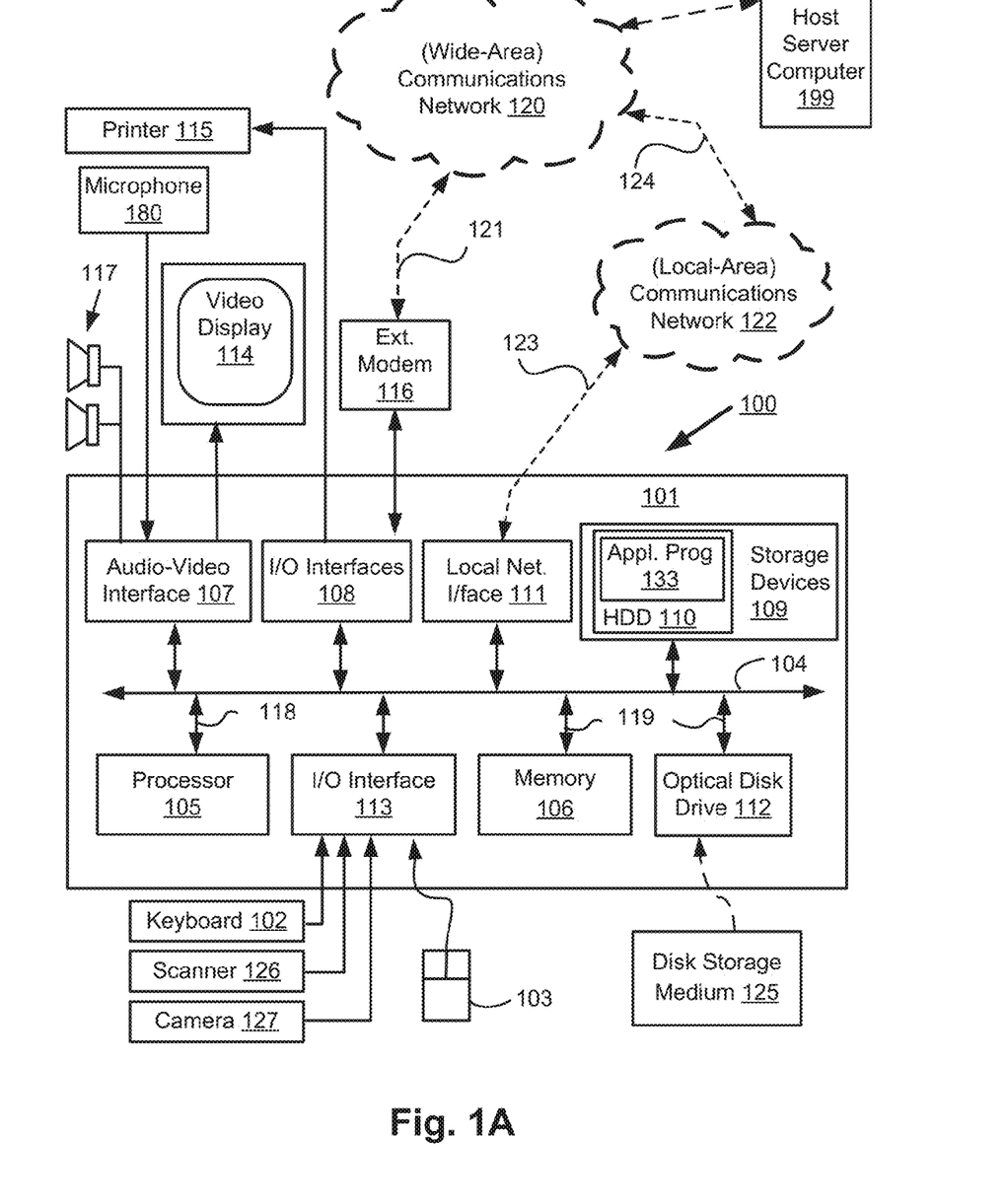
FIGS. 1A and 1B form a schematic block diagram of a general purpose computer system upon which arrangements described can be practiced.
Figure 1B:
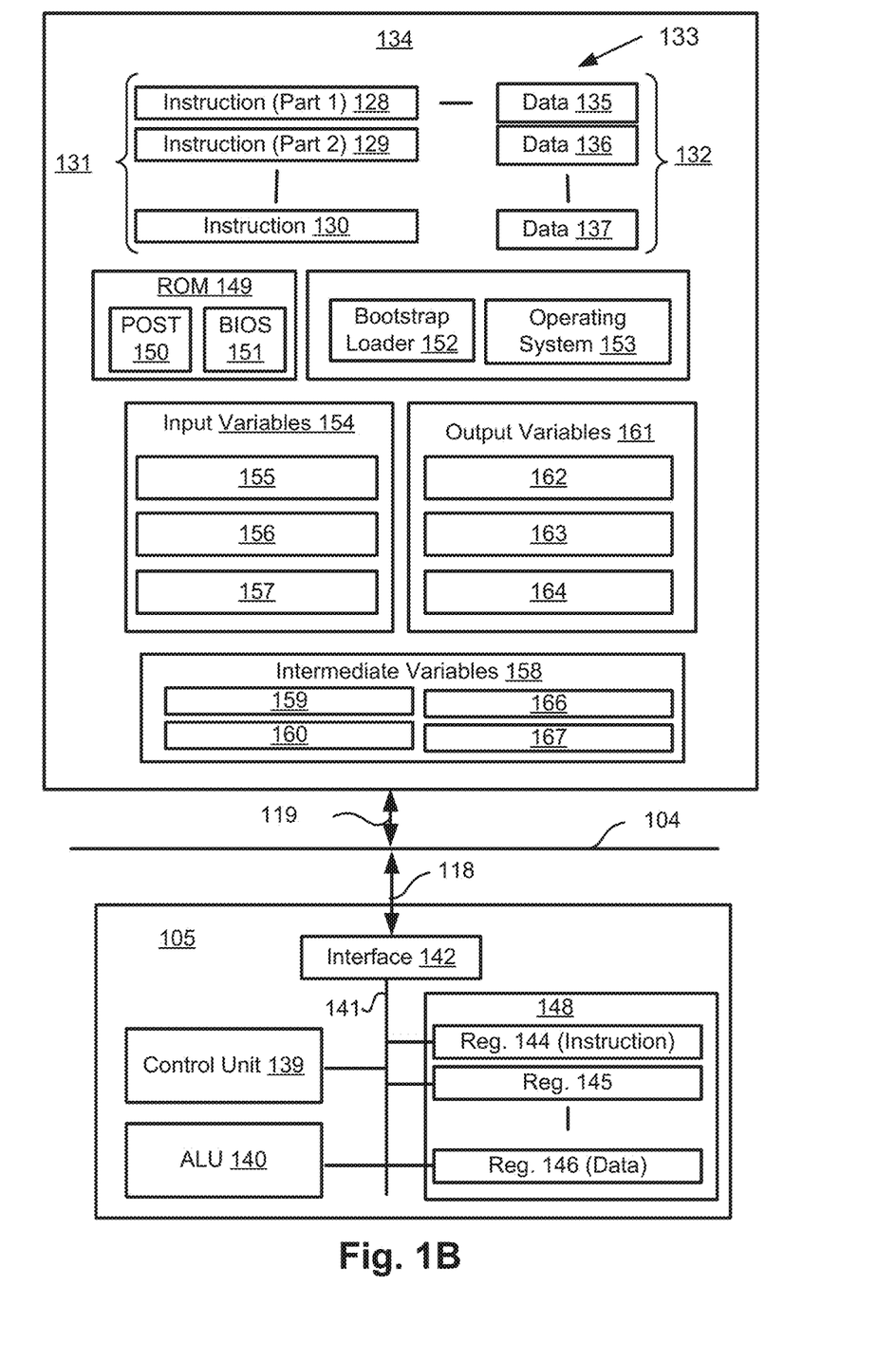

FIGS. 1A and 1B depict a general-purpose computer system 100, upon which the various arrangements to be described can be practiced.

As seen in FIG. 1A, the computer system 100 includes: a computer module 101; input devices such as a keyboard 102, a mouse pointer device 103, a scanner 126, a camera 127, and a microphone 180; and output devices including a printer 115, a display device 114 and loudspeakers 117. The display 114 is most desirably a flat panel display such as formed using plasma, LCD or LED technologies, for example. An external Modulator-Demodulator (Modem) transceiver device 116 may be used by the computer module 101 for communicating to and from a communications network 120 via a connection 121. The communications network 120 may be a wide-area network (WAN), such as the Internet, a cellular telecommunications network, or a private WAN. Typically the network 120 provides for coupling to a host server computer 199 which may be configured to supply testing programs to the computer module 101 an to receive test, or diagnosis data, or both from the computer module 101. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer module 101 typically includes at least one processor unit 105, and a memory unit 106. For example, the memory unit 106 may have semiconductor random access memory (RAM) and semiconductor read only memory (ROM). The computer module 101 also includes an number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may comprise an Ethernet™ circuit card, a Bluetooth™ wireless arrangement or an IEEE 802.11 wireless arrangement; however, numerous other types of interfaces may be practiced for the interface 111.

The I/O interfaces 108 and 113 may afford either or both of serial and parallel connectivity, the former typically being implemented according to the Universal Serial Bus (USB) standards and having corresponding USB connectors (not illustrated). Storage devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119. Examples of computers on which the described arrangements can be practised include IBM-PC's and compatibles, Sun Sparcstations, Apple Mac™ or a like computer systems.

The methods of vision testing, including the presently disclosed astigmatism testing, may be implemented using the computer system 100 wherein the processes of FIGS. 2 to 6, to be described, may be implemented as one or more software application programs 133 executable within the computer system 100. In particular, the steps of the methods of astigmatism testing are effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the astigmatism tests and a second part and the corresponding code modules manage a user interface between the first part and the user.

The software may be stored in a computer readable storage medium, including the storage devices described below, for example. The software is loaded into the computer system 100 from the computer readable medium, and then executed by the computer system 100. A computer readable storage medium having such software or computer program recorded on the computer readable medium is a computer program product. The use of the computer program product in the computer system 100 preferably effects an advantageous apparatus for vision testing, particularly astigmatism testing.

The software 133 is typically stored in the HDD 110 or the memory 106. The software is loaded into the computer system 100 from a computer readable medium, and executed by the computer system 100. Thus, for example, the software 133 may be stored on an optically readable disk storage medium (e.g., CD-ROM) 125 that is read by the optical disk drive 112. A computer readable medium having such software or computer program recorded on it is a computer program product. The use of the computer program product in the computer system 100 preferably effects an apparatus for vision testing including astigmatism testing.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any storage medium that provides recorded instructions and/or data to the computer system 100 for execution and/or processing. Examples of such storage media include floppy disks, magnetic tape, CD-ROM, DVD, Blu-ray Disc™, a hard disk drive, a ROM or integrated circuit, USB memory, a magneto-optical disk, or a computer readable card such as a PCMCIA card and the like, whether or not such devices are internal or external of the computer module 101. Examples of computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. Through manipulation of typically the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 executes. The POST program 150 is typically stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 activates the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 1105 waits for a subsequent input, to which the processor 105 reacts to by executing another set of instructions. Each input may be provided from one or more of a number of sources, including data generated by one or more of the input devices 102, 103, data received from an external source across one of the networks 120, 102, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

The disclosed vision testing arrangements use input variables 154, which are stored in the memory 134 in corresponding memory locations 155, 156, 157. The vision testing arrangements produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle comprises:

(a) a fetch operation, which fetches or reads an instruction 131 from a memory location 128, 129, 130;

(b) a decode operation in which the control unit 139 determines which instruction has been fetched; and (c) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the processes of FIGS. 2 to 6 is associated with one or more segments of the program 133 and is performed by the register section 144, 145, 147, the ALU 140, and the control unit 139 in the processor 105 working together to perform the fetch, decode, and execute cycles for every instruction in the instruction set for the noted segments of the program 133.

The astigmatism tests of FIGS. 2 to 6 are desirably configured to execute in the computer system 100 in an interactive fashion between the server 199 and the computer module 1010 over the network 120 (such as the World Wide Web), where the computer module 101 and associated components are operated by the subject of the tests. The astigmatism test should, for maximum benefit and testing procedure optimisation, be executed in sequence with the other vision tests, such as mentioned in the Background section.

Figure 4:
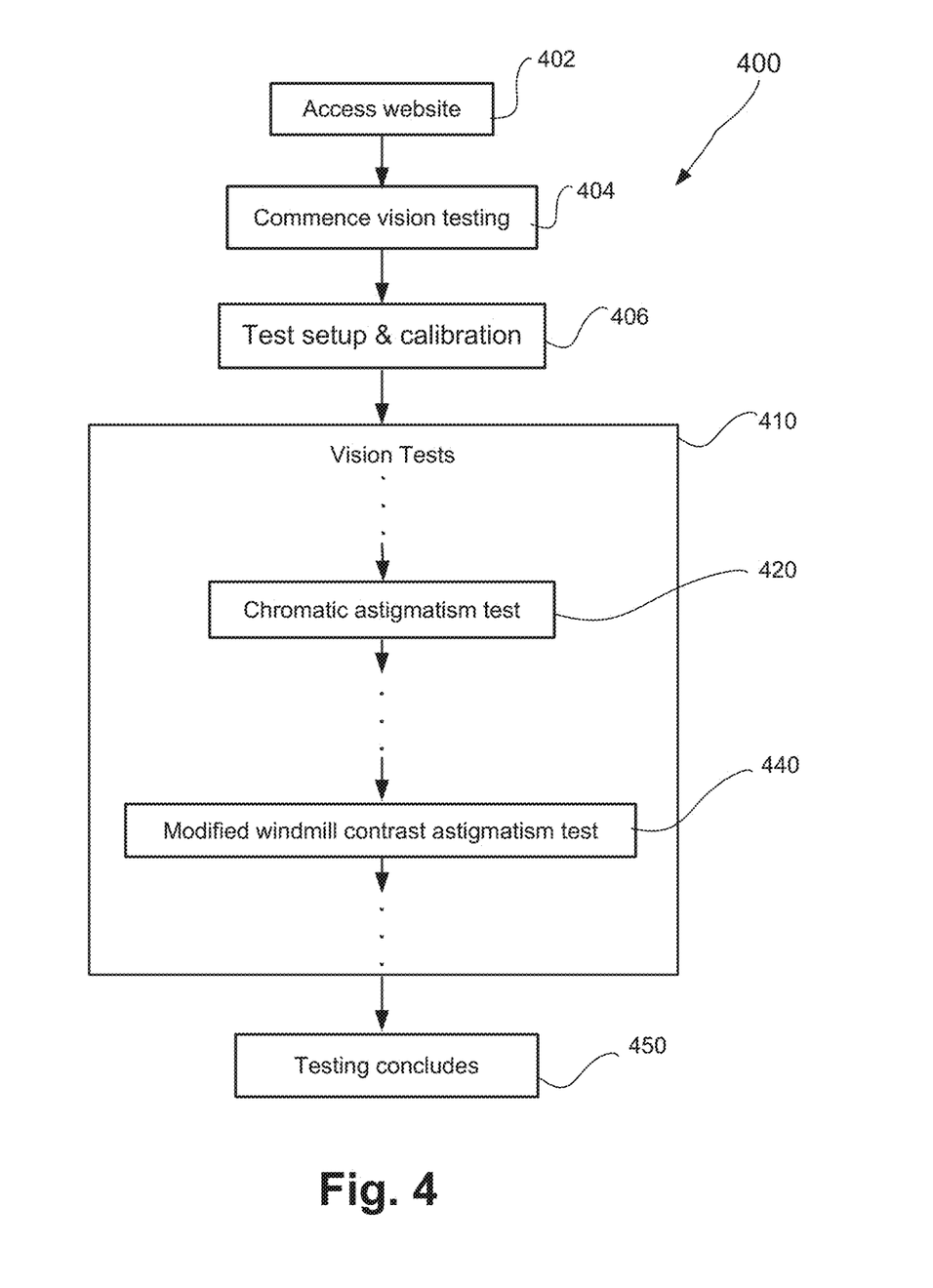
FIG. 4 is a flow chart of a method of vision testing according to the present disclosure.

Particularly, as seen in FIG. 4, in a preferred implementation, a method 400 of vision testing is performed by a subject person operating the computer module 101 and associated interfaces. Typically, the application 133 discussed above is made available as an Internet web-service and at step 402 the subject accesses an appropriate website from where the testing is made available. At step 404 vision testing may be commenced by which the server 199 downloads to the computer 101 a main program for running the testing procedure, the main program presenting the overall schema and control for the vision testing regimen. Initial execution of the main program invokes a test and calibration procedure 406 where the main program calls upon the server 199 to download to the computer 101 a test and calibration program. The test a calibration program is stored to the memory 106 and is executed by the processor to test and calibrate the optical system formed by the flat panel display 114 and the subject, who has control of the input devices 102 and 103.

Once the system is calibrated, the main program executes the vision testing regimen 410, downloading from the server 199 individual test programs for testing various aspects of eyesight of the subject. Responses of the subject may be recorded in the memory 106 or HDD 110 and reported to the server in real-time during performance of a particular test, or upon conclusion of the test. An assessment of the responses by the server 199 results in the server 199 issuing instruction to the main program to guide the testing process and to identify the next test to be performed. During the testing phase, astigmatism tests may be performed including a chromatic astigmatism test 420 and/or a modified windmill contrast astigmatism test. In each case, where such a test is performed, a sub-application for that test is downloaded from the server 199 to the computer 101 for storage and executing under control and guidance of instructions and responses input by the subject via the keyboard 102 and/or mouse pointer 103. When all testing is completed, at step 450, the main program delivers final test data to the server 199 for assessment and analysis for the formulation of an optical lens prescription for verification according to established quality control procedures.

The tests of FIGS. 2, 3, 5 and 6 have been devised to obtain a more accurate measure of the astigmatism of each of the subject's eyes. A corresponding traditional test would normally be carried out in the optometry clinic by a skilled optometrist using a series of cylindrical lenses.

When a spot is viewed by a human whose eyesight has a high refractive error, the spot appears to be defocused or blurred. Also, when a spot is defocused or blurred, the spot appears fainter and larger than its original size. When two dots are side by side and then defocused, the blur of each dot overlaps, and the dots appear to merge into one. The distance between the two dots which allows the observer to see them as two distinct points, rather than one, is related to the visual discrimination.

Consequently the visual discrimination of the human subject can be determined by measuring the separation between two objects of a fixed size at a known distance. As the refractive error increases, the visual discrimination decreases, and the distance of separation between the two objects will need to increase to enable them to be discriminated as two separate objects.

In the case of astigmatic blur, the image may be blurred in one particular orientation not another. By measuring the degree of blur at various angles between 0 and 360 degrees, it is possible to determine a position where there is minimal and maximal blur. This minimal blur orientation relates to the angle of astigmatism as classically measured while the maximal blur relates to the astigmatic power.

Chromatic Astigmatism Test

Figure 2:
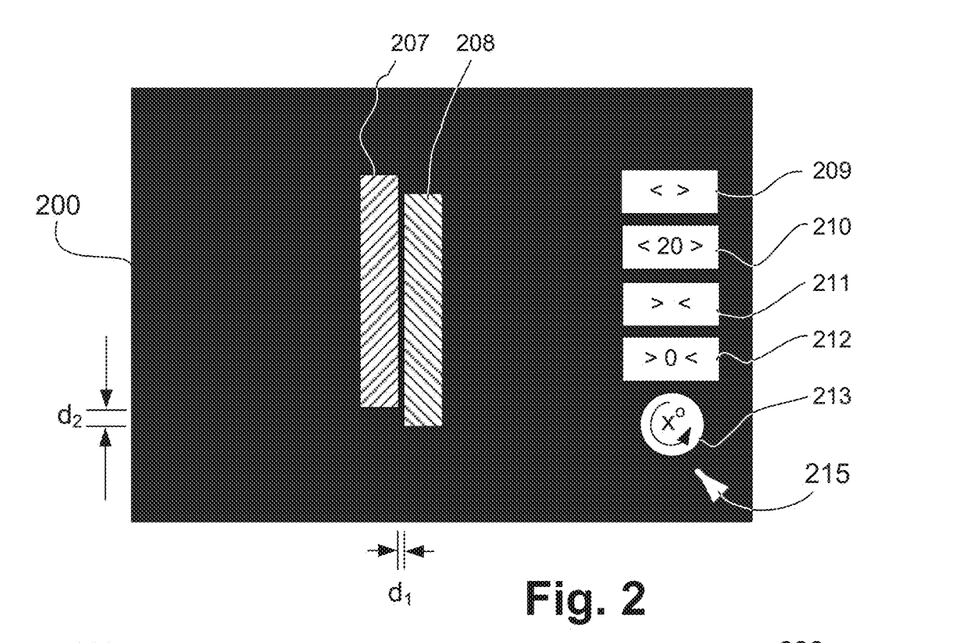
FIG. 2 shows a screen display graphical user interface of a first astigmatism test according to the present disclosure.

FIG. 2 shows a GUI 200 of the chromatic astigmatism test 420 and FIG. 4 a flowchart for a sub-program that may be used to implement the test. The GUI 200 is indicative of a screen display as reproduced by the flat panel display 114 during a testing sequence. The principle of the test is to measure the distance of separation of the blur points of two parallel elongate coloured bars 207 and 208, the distance being proportional to the degree of refractive error. The coloured bars 207, 208 are displayed against a black background (0,0,0 RGB) of the GUI 200.

The coloured rectangular bars 207, 208 as illustrated are of similar size (e.g. approximately 10×70 mm for a typically sized display screen 114, preferably 9 by 68 mm in some instances) and at least initially slightly offset, or transversely displaced, by for example, by a distance $d_1$ of 1 mm. As seen in the example of FIG. 2, the bars 207 and 208 are also longitudinally displaced by a distance $d_2$. The initial transverse displacement of the parallel bars 207 and 208 permits part of the black background to appear between the bars 207, 208. One bar, such as the bar 207, is coloured red (255, 0, 0 RGB), and the other bar 208 is coloured either blue (0,0,255 RGB) or yellow (255,255,0 RGB). The GUI 200 also includes a number of graphical buttons 209-213 selectable by the subject through manipulation of the mouse 103 and a corresponding cursor 215 seen in FIG. 2

The subjects sits at a prescribed distance, generally between 1 meter and 6 meters from the computer monitor screen 114, the distance being established and recorded during a set-up and calibration phase 406 of the overall testing sequence 400.

The test 420 can be performed by the subject alone, or with the aid of an assistant, either of whom can use the mouse 103 to vary the interval between the two bars 207, 208 as now described.

Figure 3:
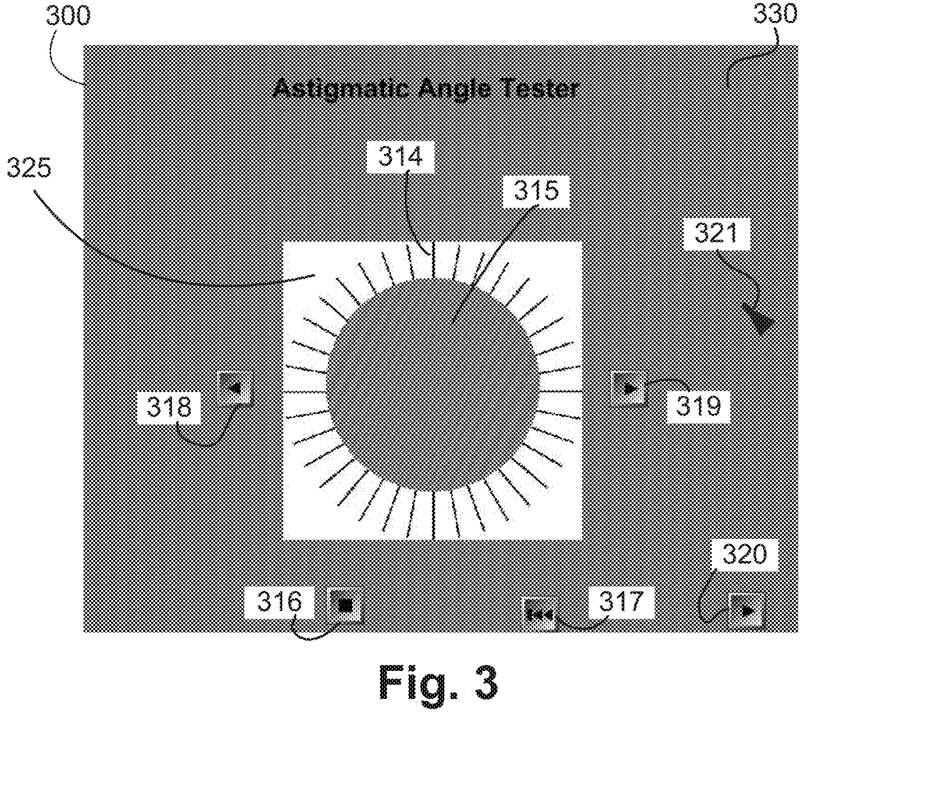
FIG. 3 shows a screen display graphical user interface of a second astigmatism test according to the present disclosure.
Figure 5:
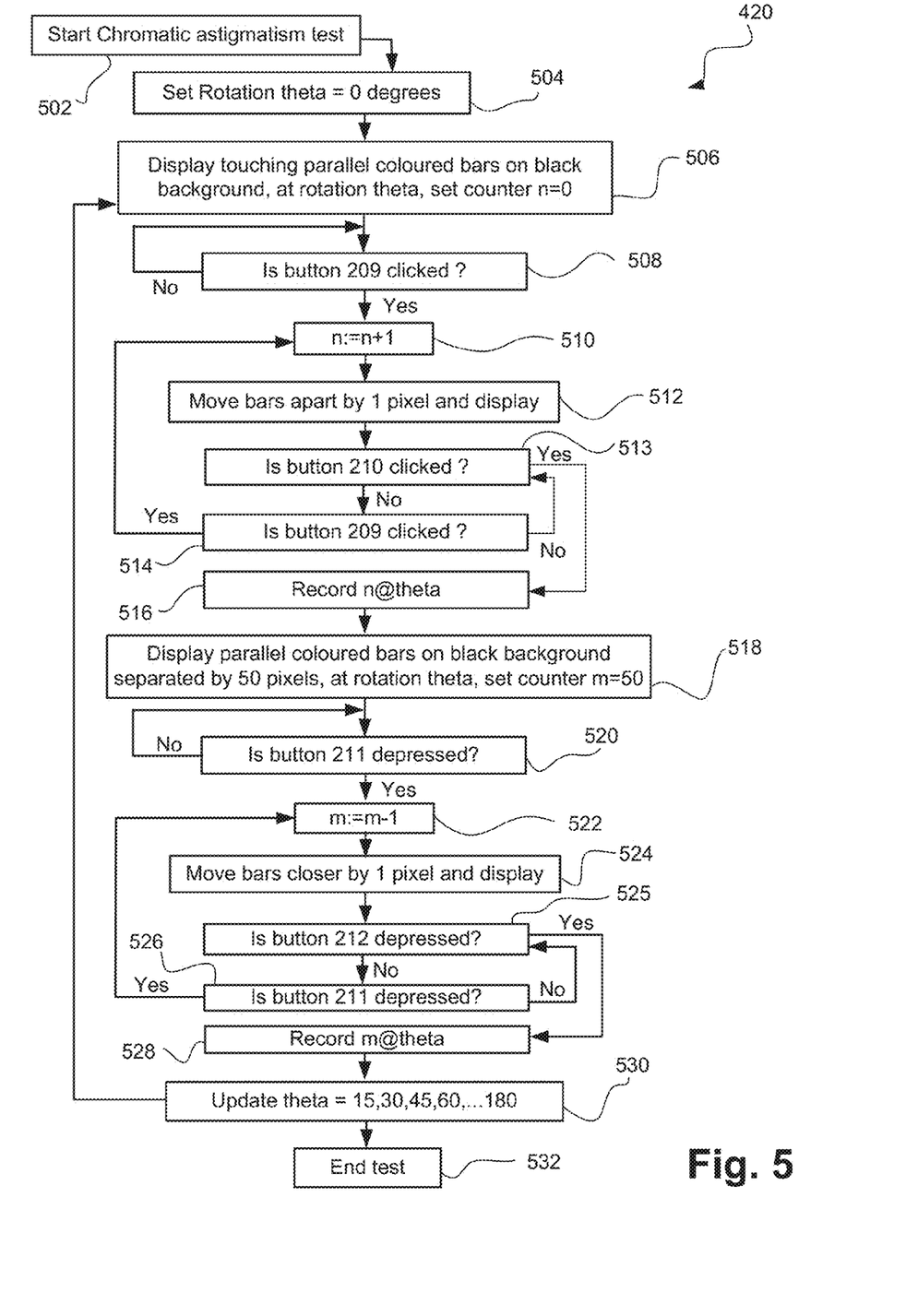
FIG. 5 is a flow chart of the method of the test of FIG. 2.

With reference to FIGS. 3 and 5, at step 502 the test 420 starts. At step 504, a rotation value theta is set to 0 degrees and in step 506 the two bars 207, 208 are initially displayed against the black background joined or touching in the vertical orientation (i.e. 0 degrees). Step 506 also sets a counter, n, to zero. The bars 207, 208 are then separated by the subject clicking or otherwise selecting an active button 209 in the GUI 200 using the cursor 215 and mouse pointer 103. The program of the test 420 in step 508 operates to detect depression of the button 209. Where the button is not pressed, the program continues to await such action by the subject. Upon detection of depression of the active button 209 in step 508, the program firstly increments the counter, n in step 510 and in step 512 executes via the GUI 200 to cause the two bars 207 and 208 to slowly separate, preferably by a distance of 1 pixel. Step 514 then checks for depression of the button 209 via the mouse 103. Where the button 209 is depressed, the program returns to step 510 where the counter, n, is incremented and step 512 moves the bars 207, 208 further apart. The button 209 is repeatedly clicked (via the mouse 103 being pressed on and released off), as detected at step 514, at a rate of about one click per second until the subject identifies that they can distinguish the separation. Consequential manipulation of the mouse 103 and cursor 215, and selection of the button 210, detected at step 513, causes the distance of separation (being the counter value n, in pixels) to be is recorded at step 516 as the break point for the angle theta.

After detecting selection of the button 210, the program 420 then in step 518 sets the bars 207, 208 to a wider separation in the GUI 200, of for example approximately 50 pixels, at the same rotation angle theta, and sets a counter, m, to the separation distance (e.g. 50). The next objective is to move the bars closer together. This is achieved by the subject repeatedly pressing on and releasing mouse button 211 at a rate of one click per second until the bars 207, 208 are perceived to be joined. This is performed by the program 420 detecting first depression of the button 211 in step 520 and consequently decrementing the counter m in step 522 and moving the bars closer, by 1 pixel for example and updating the GUI display in step 524. Step 525 tests for selection of the button 212. If not selected, step 526 detects continued depression of the button 211 resulting in the continued closing of the bars 207, 208 according to steps 522 and 524. When the join is perceived, the subject stops pressing the button 211 then presses the button 212. This is detected in step 525. The join is called the fusion point and the count 'm' is recorded in step 528 for the current angle theta.

Selection of the button 212 also resets the separation of the two bars 207, 208 back to the correct initial joined position.

In step 530, the angle theta is updated for a range of angles to be tested, preferably in 15 degree increments, from 0 to 180 degrees. Other and/or more angles may be used. Selection and maintained depression of the button 213 via the mouse 103 and cursor 215 rotates and resets the coloured bars by the preset angle. The separation processes described above may then be repeated by the program 420 looping back to step 506 to determine the break and fusion points for this new orientation of the coloured bars 207, 208.

This testing cycle is continued for several different orientations of the bars 207, 208 such that the break and fusion points are measured for a full 360 degree rotation. The recorded break and fusion points are then output at an end of test step 532 and used to calculate both the angle and power of astigmatic components of the eye.

The test is carried out for each individual eye.

Note that recording of data in the above occurs on a specific selection for that purpose by the subject.

Modified Windmill Contrast Astigmatic Test

Figure 6:
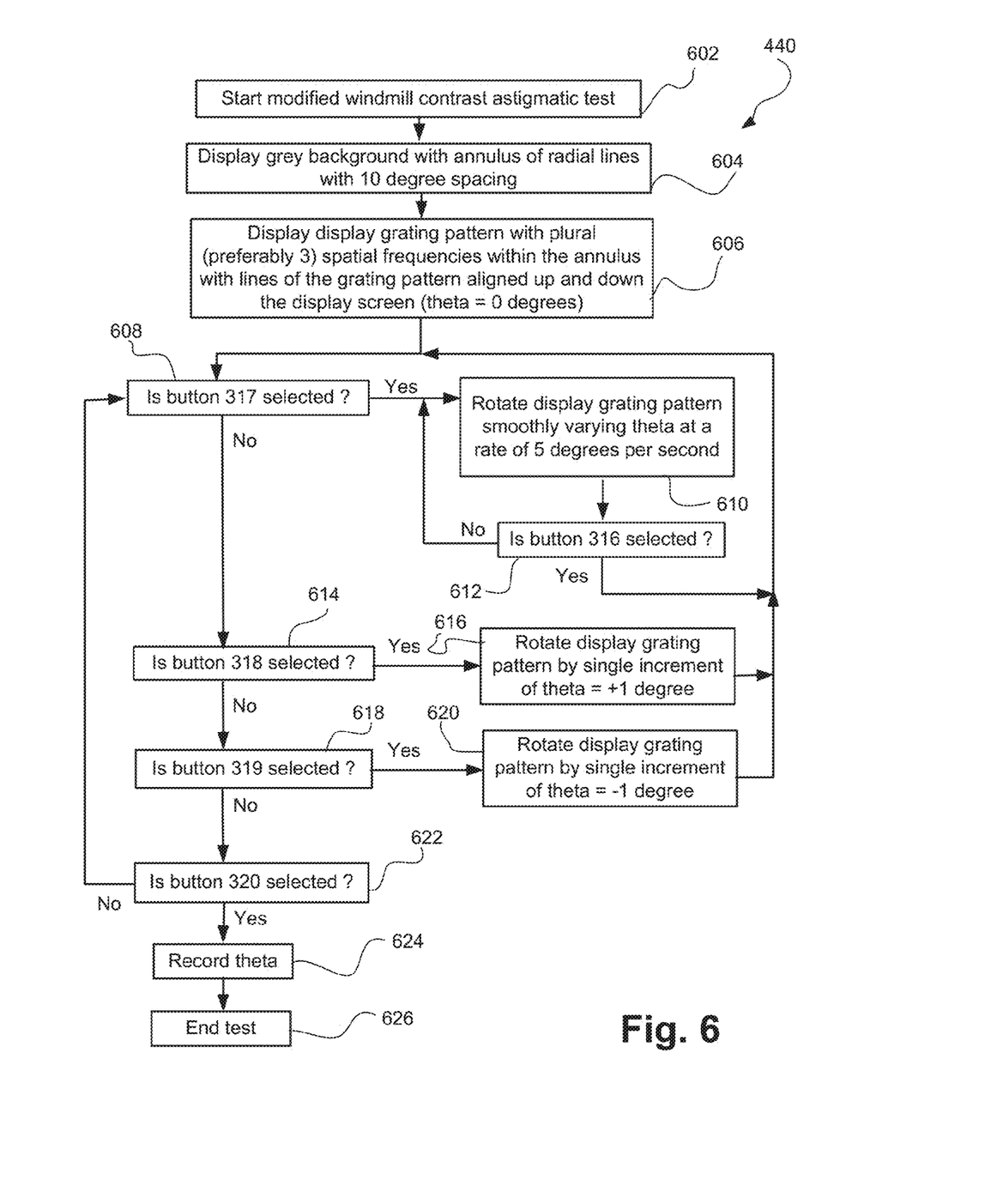
FIG. 6 is a flow chart of the method of the test of FIG. 3.

FIG. 3 shows a GUI 300 used to perform a modified windmill contrast astigmatic test 440, which is shown in schematic flow chart form, representative of a corresponding program, in FIG. 6. The GUI 300, as reproduced by the display 114, displays a number of main optical components. A first optical component is formed of an outer circle or annulus of black radial lines 314, the annulus having an inner diameter of approximately 100 mm. The radial lines 314 extend around the annulus, preferably spaced apart in 10 degree increments, and are set on a white (intermediate) background 325 (255,255,255 RBG) having a square shape.

A second optical component comprises a circular contrast grating pattern 315, formed within the annulus of radial lines 314 and over the white intermediate background 325. The circular grating pattern 315 desirably has a diameter of approximately 90 mm and is preferably centered on a grey colour (126,126,126 RGB). The contrast grating pattern 315 has three spatial frequencies, divided as follows. The middle or central third of the pattern 315 has a 12 cycle grating, and the next sixth on either side of the central third is formed using a 6 cycle frequency, and the outer sixth has a 3 cycle frequency.

A third optical component is an overall background 330 of the GUI 300, over which the white intermediate square 325 is rendered. The background 330 is formed by a linear (i.e. constant frequency) contrast grating of evenly spaced vertically aligned lines preferably centered on a grey colour (126,126,126 RGB). Due to the printer limitations or errors, when this patent specification is printed, the grating of the background 330 may in some instances interact with printer artifacts to give some amount of variation, rather than the intended linear grating. However, when viewed on a flat computer display monitor, the linear grating is readily apparent.

The grating patterns 315 and 330 may alternatively comprise shades of grey, red, or blue, observing that grey represents a combination of red, green and blue.

Figure 7:
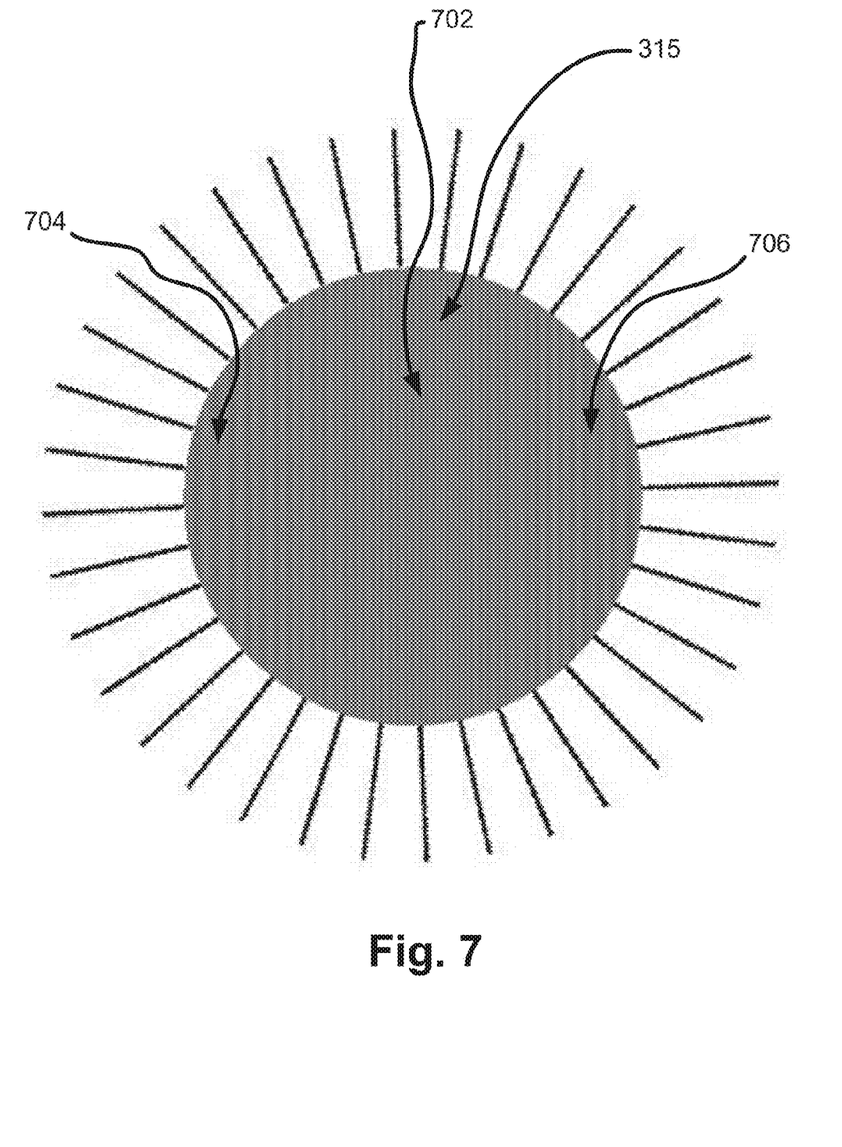
FIG. 7 is an enlargement of the grating pattern seen in FIG. 3.

By contrast, the grating patterns 315 are most desirably non-linear and intended to appear as parallel lines of varying frequency. In FIG. 3 the grating pattern 315 is inclined from the vertical, in this instance by about 30 degrees. The varying frequency is seen more clearly in FIG. 7 which shows an enlargement of the grating pattern 315 where, in this instance, the patterns are generally vertically aligned. In FIG. 7, relatively higher frequencies are at the centre 702 and relatively lower frequencies are near the edges 704 and 706. The same printer limitations discussed above may also affect the appearance of the grating 315 when this patent specification is printed.

The linear grating of the background 330 mental orientation reference for the variable grating 315, particularly when such is rotated, thus aiding interpretation of the optical interaction between the grating 315 and the radial lines 314 as perceived by the subject.

The GUI 300 has five active graphical buttons 316 to 320 which may be selected by the subject through use of the mouse pointer 103 and corresponding cursor 321. Selection of the button 317 causes smooth rotation of the inner contrast grating pattern 315 in a clockwise direction and selection of the button 316 stops the rotation. Selection of the button 318 causes the contrast grating pattern 315 to rotate in a stepped fashion one degree per step in the counter clockwise direction, to help finely adjust for the angle of astigmatism. Selection of the button 319 causes rotation of the contrast grating pattern 315 in a stepped fashion one degree at a time in the counter clockwise direction. Selection of the button 320 records the selected angle.

When a subject has astigmatism, there is a particular or optimal orientation, called the "angle of astigmatism", that will allow the subject to see images blacker and clearer. When the subject views a series of parallel lines which are pointing in the direction of the angle of astigmatism, all the lines will be clear and distinct. If the orientation moves off the optimal angle, then the lines will appear defocused, becoming less black and less clear until, at 90 degrees in the opposite direction, the lines will be fully blurred out and can fade into a faint grey colour.

Each eye is tested independently of the other.

The modified windmill contrast astigmatic test 440 commences in step 602 where the relevant sub-program is downloaded from the server 199 to the computer 101 for execution by the processor 105. The test 440 begins with the subject having one eye covered and step 604 displaying the grey background 330. Step 606 displays the contrast grating pattern aligned initially vertically (up and down), being an angle of theta=0 degrees. Step 608 then tests for selection of the button 317. Where the button 317 is selected, step 610 operates to smoothly rotate the contrast grating pattern 315, in the clockwise direction on the computer screen 114. "Smooth" rotation may, for example, be rotation at a rate of 90 degrees per second, this being sufficient for the subject to observe timely change, but not so fast that the subject has difficulty in controlling the GUI 300. As the grating pattern 315 rotates, the subject with astigmatism will notice that, in a particular orientation, the lines of the grating pattern 315 will appear well or better defined. This orientation establishes the angle of astigmatism. The subject stops the rotation of the pattern 315 when it is perceived to be near the angle of astigmatism, by selecting the button 316, this being detected at step 612. Then, using the button 318 or 319, the subject can finely adjust the orientation so that the maximum number of gratings lines are visible. For example, as seen in FIG. 6, step 614 tests if the button 614 is selected, and if so, step 616 rotates the grating 315 by a single increment of theta=+1 degree. Where the button 319 is selected, as detected in step 618, step 620 operates to rotate the grating 315 by an angle theta=−1 degree. By manipulation of the buttons 318 and 319, the subject can fine tune the angel of the grating 315 to best visibility of the grating lines. Once this is achieved, the subject uses the mouse pointer 103 and cursor 321 to select the button 320, as at step 622, to cause recording of the angle of astigmatism at step 624. The test 440 then ends at step 626 with the recorded angle (theta) being output for further processing.

When the subject experiences a large refractive error and astigmatism, it may be difficult for the subject to clearly differentiate the lines on the grating pattern 315 at any orientation. In this case the subject may observe the outer annulus of radial black lines, which will appear black and clear at the angle of astigmatism. By rotating the inner grating pattern 315, using the button 317, whilst observing the annulus lines 314, it is generally possible to perceive some of the grating frequencies of the inner grating pattern 315. Then, using the buttons 318 or 319 to finely adjust the orientation, the maximum number of gratings lines should be visible. Selection of the button 320 again will cause recording of the angle of astigmatism.

INDUSTRIAL APPLICABILITY

The arrangements described are applicable to the computer and data processing industries and particularly for the computerised vision testing of human individuals.

The foregoing describes only some embodiments of the present invention, and modifications and/or changes can be made thereto without departing from the scope and spirit of the invention, the embodiments being illustrative and not restrictive.

We claim:

1. A computer implemented method of testing astigmatism of a subject, said method comprising:
displaying on a display device a graphical user interface including a plurality of differently coloured parallel bars in an initial position against a contrasting background;
controlling movement of the bars from the initial position to cause at least one of a separation of the bars and joining of the bars;
detecting an indication of the subject of separation and joining of the bars respectively; and
recording a measure of movement of the bars from the initial position to the detected indication.

2. A method according to claim 1, wherein an initial position of the bars associated with separation is the bars touching, and an initial position of the bars associated with joining is separated by a predetermined distance.

3. A method according to claim 1 wherein one said bar is red, and one other bar is one of blue and yellow.

4. A method according to claim 1, wherein the contrasting background is black.

5. A method according to claim 1, wherein the method is repeated for each of a plurality of angles of orientation of the bars relative to the display device, said method further comprising recording the respective distances for each angle of orientation.

6. A method according to claim 1, wherein the method comprises controlling movement of the bars for each of testing separation and joining.

7. A computer implemented method of testing astigmatism of a subject, said method comprising:
displaying on a display device a graphical user interface including:
(i) an annulus of radial lines against a contrasting background, and
(ii) a circular contrast grating pattern within the annulus of radial lines;
controlling an angle of rotation of the circular grating pattern within the annulus;
detecting an indication of a maximal contrast between the circular grating pattern and the annulus of radial lines; and
recording the angle of rotation corresponding to the detected indication as the angle of astigmatism of the subject.

8. A method according to claim 7 wherein the circular grating pattern comprises a plurality of grating frequencies.

9. A method according to claim 8 wherein the circular grating pattern comprises three spatial frequencies.

10. A method according to claim 9 wherein the spatial frequencies comprise a central third of the pattern having a 12 cycle grating, and the next sixth on either side of the central third being formed using a 6 cycle frequency, and the outer sixth having a 3 cycle frequency.

11. A method according to claim 7, wherein the radial lines of the annulus are black.

12. A method according to claim 7, wherein the contrasting background is white.

13. A method according to claim 7, wherein the circular grating pattern comprises shades of grey, red, or blue.

14. A method according to claim 7, wherein the contrasting background is an intermediate background and is set against a background having a linear contrast grating.

15. A non-transitory computer readable storage medium having a computer program recorded thereon, the program being executable by a computer to implement a method to test astigmatism of a subject, said method comprising:
displaying on a display device a graphical user interface including a plurality of differently coloured parallel bars in an initial position against a contrasting background;

controlling movement of the bars from the initial position to cause at least one of a separation of the bars and joining of the bars;

detecting an indication of the subject of separation and joining of the bars respectively; and recording a measure of movement of the bars from the initial position to the detected indication.

16. A non-transitory computer readable storage medium according to claim 15, wherein the method further comprises:

displaying on a display device a graphical user interface including:
  (i) an annulus of radial lines against a contrasting background, and
  (ii) a circular contrast grating pattern within the annulus of radial lines;

controlling an angle of rotation of the circular grating pattern within the annulus;

detecting an indication of a maximal contrast between the circular grating pattern and the annulus of radial lines; and recording the angle of rotation corresponding to the detected indication as the angle of astigmatism of the subject.

17. A computer system for vision testing, said system comprising computer apparatus having a processor and a memory, the memory having recorded thereon a program executable by the processor configured to implement a method to test astigmatism of a subject, said method comprising at least one of:

(1) displaying on a display device a graphical user interface including a plurality of differently coloured parallel bars in an initial position against a contrasting background;

controlling movement of the bars from the initial position to cause at least one of a separation of the bars and joining of the bars;

detecting an indication of the subject of separation and joining of the bars respectively; and recording a measure of movement of the bars from the initial position to the detected indication; and (2) displaying on a display device a graphical user interface including:
  (i) an annulus of radial lines against a contrasting background, and
  (ii) a circular contrast grating pattern within the annulus of radial lines;

controlling an angle of rotation of the circular grating pattern within the annulus;

detecting an indication of a maximal contrast between the circular grating pattern and the annulus of radial lines; and recording the angle of rotation corresponding to the detected indication as the angle of astigmatism of the subject.

* * * * *